United States Patent [19]
Shoberg et al.

[11] Patent Number: 5,876,430
[45] Date of Patent: Mar. 2, 1999

[54] METHOD TO STIFFEN AND PROVIDE ABRASION TO CONNECTOR END OF LEADS

[75] Inventors: Bret R. Shoberg, Corcoran; David G. Schaenzer, Minneapolis, both of Minn.

[73] Assignee: Medtronic, Inc., Minneapolis, Minn.

[21] Appl. No.: 992,593

[22] Filed: Dec. 17, 1997

[51] Int. Cl.⁶ .................................................. A61N 1/05
[52] U.S. Cl. ............................................................ 607/122
[58] Field of Search ...................... 607/115, 116, 607/117, 119, 121, 122, 123, 124, 129, 133, 134, 135, 37

[56] References Cited

U.S. PATENT DOCUMENTS

| | | |
|---|---|---|
| 3,737,579 | 6/1973 | Bolduc . |
| 4,951,687 | 8/1990 | Ufford et al. . |
| 4,971,070 | 11/1990 | Holleman et al. . |
| 5,246,014 | 9/1993 | Williams et al. . |
| 5,584,873 | 12/1996 | Shoberg et al. . |

*Primary Examiner*—William F. Kamm
*Attorney, Agent, or Firm*—Reed A. Duthler; Harold R. Patton

[57] ABSTRACT

An implantable medical electrical lead having a lead body including a stranded or cabled conductor extending therein and an electrical connector mounted to a proximal end of the lead body and coupled to the stranded or cabled conductor and having a fabric tube molded into a proximal portion of the lead body adjacent the electrical connector. The fabric may be a polyester mesh formed or rolled into a tube and is preferably molded into the proximal portion of said lead body adjacent its exterior surface. The proximal portion of the lead body may be fabricated of silicone rubber or polyurethane.

7 Claims, 2 Drawing Sheets

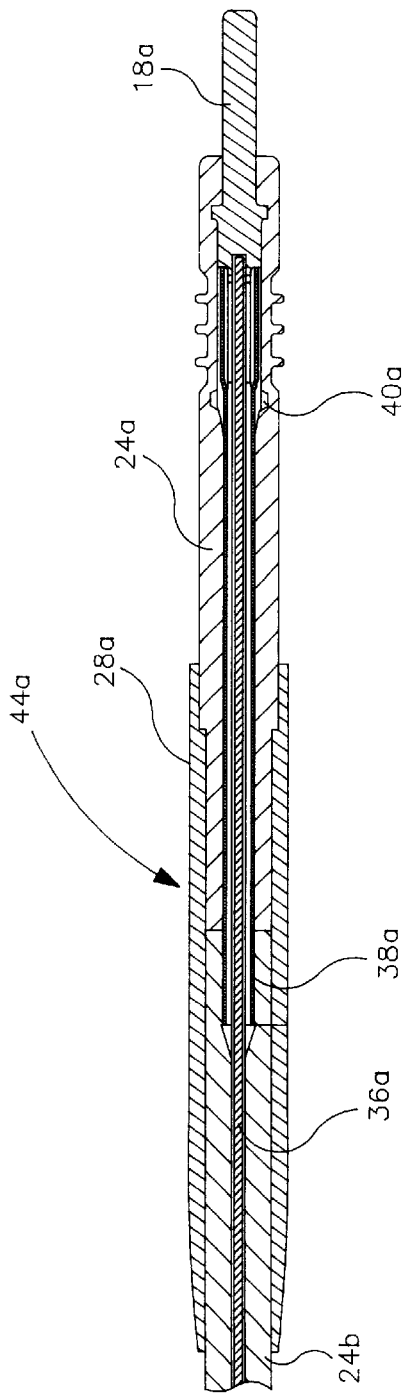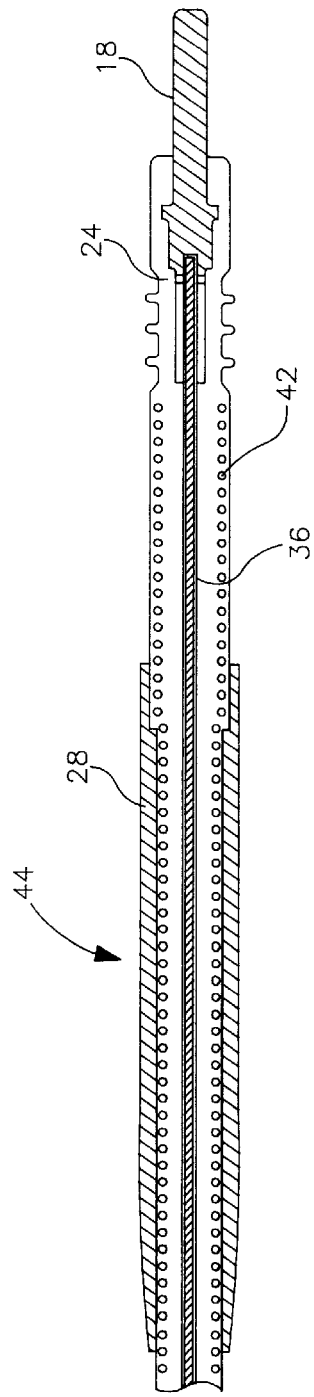

METHOD TO STIFFEN AND PROVIDE ABRASION TO CONNECTOR END OF LEADS

BACKGROUND OF THE INVENTION

The present invention relates to catheters and leads generally, and more particularly to implantable electrode leads for connection to an implantable pulse generator or monitoring device.

Implantable leads are used in conjunction with implantable stimulators and monitoring devices to carry electrical signals to the devices and stimulus pulses from the devices to body tissue. Rather than being manufactured as a single device, the electrode leads are typically manufactured as separate devices, requiring that they be interconnected with the implantable medical device. Typically, this interconnection has been by means of a connector assembly located on the proximal end of the electrode lead which is inserted into a connector bore located in the medical device.

At present, electrical connectors for use in conjunction with cardiac pacemakers and their associated leads generally correspond to the IS-1 connector standard. As an example of a lead connector meeting the IS-1 connector standard can be seen in U.S. Pat. No. 4,951,687 issued to Ufford et al. and incorporated by reference herein in its entirety. Connector assemblies for use in conjunction with implantable defibrillators, and in particular for use in conjunction with high energy cardioversion and defibrillation electrodes may correspond to the "DF-1" configuration, presently employed on Cardioverter/defibrillator leads as manufactured by Medtronic, Inc. In conjunction with connectors having the above configurations, sealing rings are provided on the connector assemblies which serve to seal the connector bores from fluid entry and to seal the connector bores between the electrical connectors coupled to the electrodes located on the lead. Insertion of the leads into the connector bores thus creates a certain amount of frictional resistance, in turn requiring that the proximal portion of the lead be configured in such a fashion that it is possible for the physician to push the lead into the connector socket.

Traditionally, cardiac pacing leads have employed conductors taking the form of monofilar or multifilar metal coils, which by their nature substantially stiffen the portion of the lead through which they pass. However, more recently designed implantable pacing and defibrillation leads may employ cabled conductors of the sort described in U.S. Pat. No. 5,246,014 issued to Williams et al. and U.S. Pat. No. 5,584,873 issued to Shoberg et al., both incorporated by reference in their entireties. Such conductors do not significantly add to the stiffness of the lead body, rendering the lead body carrying these conductors relatively more flexible than a corresponding lead body with the same number of coiled conductors. This in turn may render the proximal end of the lead more difficult to insert into the associated connector bore in the implantable stimulator or monitor with which the lead is intended to be used.

Prior leads employing cabled conductors have employed two basic mechanisms in order to assist the physician in inserting the proximal end of the lead into the connector bore of the associated device. The first mechanism is a provision of a coil or tube, mounted within the lead body and extending distally from the proximal end of the lead body which provides the proximal end of the lead body with increased column strength and some increase in rigidity to assist insertion of the connector assembly on the lead into the connector bore of the associated device. The second mechanism has then the provision of a tubular stress relief sleeve, mounted over a proximal portion of the lead body, which the physician may grasp when inserting the lead.

A second set of problems associated with the construction of the proximal portion of the lead body is that these portions of the lead body typically lie adjacent the implantable stimulator or monitor, in the subcutaneous pocket in which the device is implanted. In such case, the proximal portions of the lead body have the potential of repeatedly rubbing against the housing of the implanted device, carrying with it the potential problem of abrasion of the lead body and possible exposure of one or more of the conductors therein. This problem becomes more significant in the case of devices which are provided with porous or roughened surfaces, for example, by bead blasting as disclosed in U.S. Pat. No. 5,673,473 issued to Johnson et al, also incorporated herein by reference in its entirety.

SUMMARY OF THE INVENTION

The present invention provides a simplified construction for the proximal portion of an implantable lead adjacent the electrical connector assembly located thereon which provides both for increased column strength and eased insertion of the lead into the connector block and increased resistance to abrasion which might result from rubbing of the lead body against the associated implantable stimulator or monitor. The present invention accomplishes these goals by means of a fabric mesh, molded into the lead body along a proximal portion thereof. The fabric mesh may be a polyester mesh of the type presently employed to reinforce implantable defibrillation electrodes and to encourage tissue ingrowth in conjunction with implantable pacing electrodes, also well known for numerous other uses in conjunction with implantable medical devices. The polyester mesh is preferably molded into the lead body at or adjacent to its surface, so that the polyester mesh may assist in preventing abrasion of the lead body due to rubbing of the lead body against the housing of the associated medical device. Preferably, the mesh extends from the connector assembly distally for a distance sufficient to assure that that portion of the lead which might rub against the device housing is protected, but not so far distally as to extend out of the pocket in which the device is implanted. For example, in the case of a device employing a bifurcated connector, the reinforcing mesh may extend distally to approximately the point of the bifurcation.

BRIEF DESCRIPTION OF THE DRAWINGS

FIG. 2 is a sectional view of a prior art lead corresponding generally to that issued in FIG. 1, but not employing the present invention.

FIG. 3 is a sectional view through one of the connector assemblies of the lead illustrated in FIG. 1, employing the present invention.

DETAILED DESCRIPTION OF THE PREFERRED EMBODIMENT

Figure 1:
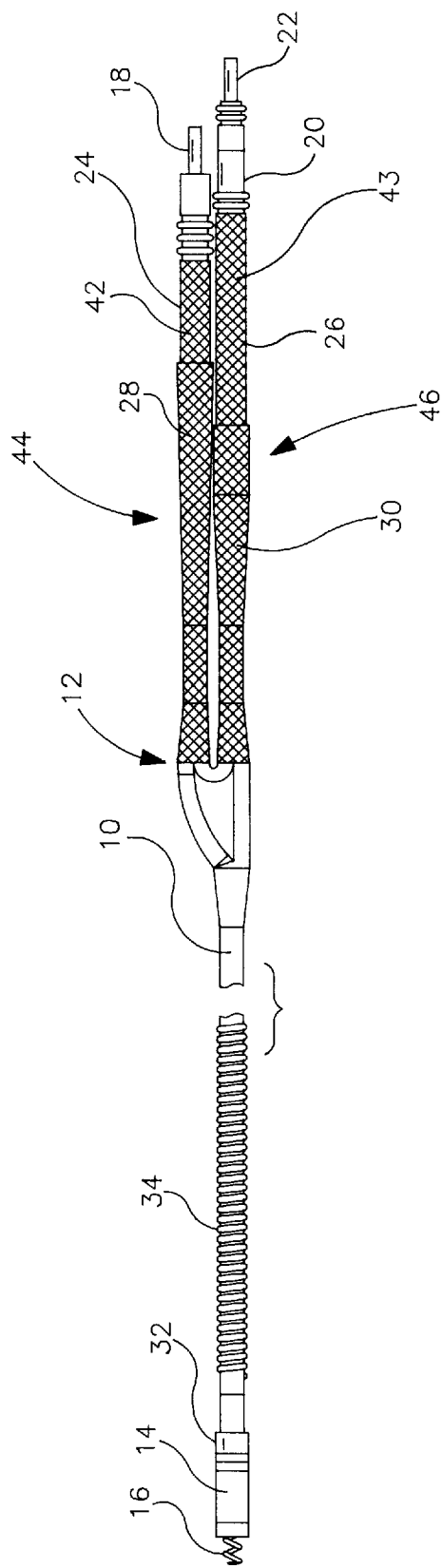
FIG. 1 is a plan view of a lead according to the present invention.

FIG. 1 is a plan view of an implantable pacing/cardioversion/defibrillation lead. The lead is provided with an elongated lead body 10 which at its proximal end carries a connector assembly including two connector arms 44 and 46 extending from a bifurcation sleeve 12. The first connector arm 44 carries a single connector pin 18, coupled by means of a stranded or cabled conductor to cardioversion/ defibrillation electrode 34. A molded strain relief sleeve 28 surrounds proximal lead body segment 24. Similarly, the second connector arm 46 includes a molded strain relief sleeve 30, surrounding proximal lead body segment 26. The second connector arm 46 carries a connector ring 20 coupled by means of a stranded or cabled conductor to ring electrode 32 and a connector pin 22 coupled to helical electrode 16, typically by means of a coiled conductor. Connector pin 22 may be rotated, rotating the coiled conductor therein to advance electrode 16 out of electrode head 14 according to the teaching of U.S. Pat. No. 4,106,512 issued to Bisping, incorporated herein by reference in its entirety.

Lead body 10 may be fabricated of silicone rubber or polyurethane and may, for example, take the form of a multi-lumen lead body of the sort illustrated in the above cited Shoberg et al. patent. Proximal lead body segments 24 and 26 are preferably fabricated of silicone rubber, with strain relief sleeves 28 and 30 being fabricated of either polyurethane or silicone rubber. Molded within proximal lead body portions 24 and 26 are tubular reinforcement meshes 42 and 43, which are located close to or at the surface of proximal lead body segments 24 and 26. Meshes 42 and 43 may be polyester meshes of the type typically used to reinforce implantable cardioversion and defibrillation electrodes as described in U.S. Pat. No. 4,971,070 issued to Holleman et al. and U.S. Pat. No. 3,737,579, issued to Bolduc, both incorporated herein by reference in their entireties. In particular, the mesh may take the form of a polyester surgical mesh of the type manufactured by DuPont or its equivalent. Alternatively, a woven or braided fabric of similar characteristics may be substituted.

FIG. 2 is a sectional view through the proximal portion of a first prior art connector arm 44a, corresponding in external configuration to connector arm 44 illustrated in FIG. 1. Connector arm 44a comprises a molded plastic proximal lead body portion comprising two separately formed members 24a and 24b, member 24b taking the form of a pre-formed silicone rubber tube, with lead body portion 24a molded in situ around the components included therein, including connector pin 18a, strain relief coil 38a and crimping sleeve 40a which couples strain relief sleeve 38a to connector pin 16a. Mounted external to the lead body portions 24a and 24b is a strain relief sleeve 28a which may also be fabricated of silicone rubber. Stranded or cabled conductor 36a extends through the proximal lead body and is coupled to connector pin 18a.

FIG. 3 illustrates a sectional view through the proximal portion of first connector arm 44 illustrated in FIG. 1. First connector arm 44 includes a molded proximal lead body portion 24 which is in situ molded around connector pin 18 and stranded or cabled conductor 32 and extends distally to bifurcation sleeve 12 (FIG. 1). Mounted external to proximal lead body portion 24 is a strain relief sleeve 28.

Visible in cross-section is fabric mesh 42, which may take the form of a polyester mesh as described above. As shown, polyester mesh 42 is molded into proximal lead body 24 closely adjacent the exterior surface of the lead body. Mesh 42 may take the form of a tubular polyester mesh or a strip of polyester mesh rolled into a tube and placed into a mold along with connector pin 18 and conductor 36, with silicone rubber thereafter injected into the mold under pressure in order to form proximal lead body portion 24. After curing, bifurcation sleeve 12 (FIG. 1) may thereafter be in situ molded around the proximal end of proximal lead body portion 24 and around the distal end of lead body 10 (FIG. 1) to complete the assembly of the lead.

In conjunction with the above disclosure, we claim:

1. An implantable medical electrical lead comprising:
   an elongated insulative lead body;
   a stranded or cabled conductor extending within said lead body;
   an electrical connector mounted to a proximal end of said lead body and coupled to said conductor; and
   a fabric tube molded into a proximal portion of said lead body adjacent said electrical connector.

2. A lead according to claim 1 wherein said fabric comprises a polyester mesh.

3. A lead according to claim 1 wherein said tube of fabric is a sheet of polyester mesh rolled into a tube.

4. A lead according to claim 1 or claim 2 wherein said tube is molded into said proximal portion of said lead body adjacent an exterior surface of said portion.

5. A lead according to claim 1 or claim 2 wherein said tube is molded into said proximal portion of said lead body at an exterior surface of said portion.

6. A lead according to claim 1 or claim 2 wherein said tube of fabric is a sheet of said fabric rolled into a tube.

7. A lead according to claim 1 or claim 2 wherein said proximal portion of said lead body is fabricated of silicone rubber or polyurethane.

* * * * *